(12) United States Patent
Wong et al.

(10) Patent No.: US 12,329,918 B2
(45) Date of Patent: Jun. 17, 2025

(54) NEEDLE COVER RETENTION (71) Applicant: Becton, Dickinson and Company, Franklin Lakes, NJ (US)

(72) Inventors: Yun Hui Wong, Singapore (SG); Ralph L. Sonderegger, Farmington, UT (US); Shaun Staley, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/337,159

(22) Filed: Jun. 2, 2021

(65) Prior Publication Data

US 2021/0379339 A1 Dec. 9, 2021

Related U.S. Application Data (60) Provisional application No. 63/036,872, filed on Jun. 9, 2020.

(51) Int. Cl.
*A61M 25/06* (2006.01)

(52) U.S. Cl.
CPC ..... *A61M 25/0618* (2013.01); *A61M 25/0606* (2013.01)

(58) Field of Classification Search
CPC .......... A61M 25/0606; A61M 25/0612; A61M 25/0043; A61M 25/0618; A61M 5/3202; A61M 2025/0098
See application file for complete search history.

(56) References Cited

U.S. PATENT DOCUMENTS

| 3,390,759 | A | * | 7/1968 | Vanderbeck | ........ A61M 5/3202 206/365 |
| 11,612,723 | B2 | | 3/2023 | Sonderegger et al. | |
| 2003/0125713 | A1 | * | 7/2003 | McGlinch | ............. A61F 2/0095 604/533 |
| 2005/0004532 | A1 | | 1/2005 | Woehr et al. | |
| 2005/0061697 | A1 | * | 3/2005 | Moberg | ................ A61F 2/0095 206/364 |
| 2007/0049868 | A1 | | 3/2007 | Woehr et al. | |
| 2007/0083159 | A1 | | 4/2007 | Woehr et al. | |
| 2010/0087787 | A1 | | 4/2010 | Woehr et al. | |
| 2013/0150807 | A1 | | 6/2013 | Hamuro et al. | |
| 2014/0276397 | A1 | | 9/2014 | Terwey | |
| 2018/0318557 | A1 | * | 11/2018 | Burkholz | .............. A61M 39/10 |

(Continued)

FOREIGN PATENT DOCUMENTS

| AT | 285807 T | 1/2005 |
| AU | 2002301586 B2 | 12/2009 |

(Continued)

*Primary Examiner* — Joel M Attey
*Assistant Examiner* — Antarius S Daniel
(74) *Attorney, Agent, or Firm* — Kirton McConkie; Whitney Blair; Kevin Stinger (57) ABSTRACT

A catheter system may include a catheter adapter, which may include a body and a nose extending distally from the body. The nose may be generally cylindrical. A strain relief rib may be disposed on the nose. The strain relief rib may be constructed of a flexible material. A bump may be disposed on the strain relief rib and configured to contact a needle cover. A catheter may be secured within the catheter adapter and extend distally beyond the nose.

19 Claims, 7 Drawing Sheets

(56) References Cited

U.S. PATENT DOCUMENTS

| | | | |
|---|---|---|---|
| 2020/0164180 | A1 | 5/2020 | Sonderegger et al. |
| 2021/0085920 | A1* | 3/2021 | Roberts ............. B29C 45/14336 |
| 2021/0379294 | A1* | 12/2021 | Pouget ................ A61M 5/3202 |

FOREIGN PATENT DOCUMENTS

| | | | |
|---|---|---|---|
| AU | 2010200895 | A1 | 4/2010 |
| AU | 2018261521 | | 4/2019 |
| AU | 2019387215 | A1 | 7/2021 |
| BR | 112019022075 | A2 | 5/2020 |
| BR | 112021009760 | A2 | 8/2021 |
| CA | 2409306 | A1 | 4/2003 |
| CA | 3038151 | A1 | 11/2018 |
| CA | 3119592 | A1 | 6/2020 |
| CN | 103157168 | A | 6/2013 |
| CN | 108785829 | A | 11/2018 |
| CN | 208785540 | U | 4/2019 |
| CN | 209645575 | U | 11/2019 |
| CN | 113164715 | A | 7/2021 |
| CN | 113730767 | A | 12/2021 |
| DE | 60202426 | T2 | 4/2006 |
| EP | 1306097 | | 5/2003 |
| EP | 1518576 | A2 | 3/2005 |
| EP | 1518577 | A2 | 3/2005 |
| EP | 1518578 | A2 | 3/2005 |
| EP | 1520598 | A2 | 4/2005 |
| EP | 2604306 | A1 | 6/2013 |
| EP | 2777740 | A2 | 9/2014 |
| EP | 3618912 | A2 | 3/2020 |
| EP | 3886967 | A | 10/2021 |
| ES | 2236421 | T3 | 7/2005 |
| JP | 2003180829 | A | 7/2003 |
| JP | 2010000388 | A | 1/2010 |
| JP | 4741165 | B2 | 8/2011 |
| JP | 5036779 | B2 | 9/2012 |
| JP | 2013121461 | A | 6/2013 |
| JP | 5908270 | B2 | 4/2016 |
| JP | 2016527027 | A | 9/2016 |
| JP | 2018520722 | A | 8/2018 |
| JP | 2019536540 | A | 12/2019 |
| JP | 6785963 | B2 | 11/2020 |
| KR | 20210095902 | A | 8/2021 |
| SG | 11201902690 | Y | 11/2019 |
| SG | 11202104698 | S | 6/2021 |
| WO | 2010/061405 | | 6/2010 |
| WO | 2013/141347 | | 9/2013 |
| WO | 2017074682 | A1 | 5/2017 |
| WO | 2018204636 | A2 | 11/2018 |
| WO | 2020112892 | A1 | 6/2020 |

* cited by examiner

NEEDLE COVER RETENTION

RELATED APPLICATIONS

This application claims benefit of U.S. Provisional Patent Application No. 63/036,872, filed on Jun. 9, 2020, entitled NEEDLE COVER RETENTION, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and the introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

There is a risk of accidental needle sticks if the distal tip of the introducer needle is not secured properly in a needle cover or shield. However, removal of a secured needle cover from the PIVC catheter assembly can pose a needle-stick-threat to the clinician if a large force is used by the clinician to remove the needle cover. The present disclosure presents systems and methods to significantly limit and/or prevent needle sticks. The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, a catheter system may include a catheter assembly and a needle assembly coupled to the catheter assembly. In some embodiments, the needle assembly may include a needle hub and an introducer needle. In some embodiments, a proximal end of the introducer needle may be secured within the needle hub.

In some embodiments, the catheter assembly may include a catheter adapter, which may include a body and a nose extending distally from the body. In some embodiments, the catheter assembly may include a catheter secured within the catheter adapter and extending distally beyond the nose. In some embodiments, the catheter may include a peripheral intravenous catheter (PIVC), a midline catheter, or a peripherally-inserted central catheter.

In some embodiments, the introducer needle may extend through the catheter. In some embodiments, in response to the introducer needle and/or the catheter being inserted into vasculature of a patient, the introducer needle may be proximally withdrawn from the catheter and removed from the catheter assembly. In some embodiments, the catheter may remain within the vasculature of the patient for blood draw and/or fluid infusion.

In some embodiments, the nose may be generally cylindrical. In some embodiments, the nose may be constructed of a rigid or semi-rigid material. In some embodiments, a strain relief rib may be disposed on the nose. In some embodiments, the strain relief rib may be generally aligned with a longitudinal axis of the catheter system. In some embodiments, a bump and/or another bump may be disposed on the strain relief rib.

In some embodiments, the strain relief rib may be constructed of a compliant or flexible material. In some embodiments, the bump and/or the other bump may be constructed of the flexible material or another suitable flexible material. In some embodiments, a distal end of the nose may include a strain relief element at least partially surrounding the catheter and constructed of the flexible material or another suitable flexible material. In some embodiments, the flexible material may include an elastomer, such as a thermoplastic elastomer or another suitable elastomer. In some embodiments, one or more of the following may be monolithically formed as a single unit: the strain relief rib, the bump, the other bump, and the strain relief element.

In some embodiments, the bump may be aligned with the other bump. In some embodiments, the bump may be distal to the other bump. In some embodiments, a distal end of the bump may include a first side and a second side. In some embodiments, the first side and the second side may be proximate the strain relief rib. In some embodiments, the first side and the second side may be angled toward each other, such that the distal end of the bump is tapered in a distal direction, which may facilitate lead-in or smooth movement of a needle cover with respect to the catheter assembly.

In some embodiments, the distal end of the bump may be tapered in the distal direction toward a central axis of the bump, which may be aligned with the longitudinal axis of the catheter system. In some embodiments, a height of the distal end of the bump may decrease in the distal direction. In some embodiments, one or more of the following may be disposed on a bottom of the catheter assembly: the strain relief rib, the bump, and the other bump. In some embodiments, a bevel of the introducer needle may face upwardly, away from the bottom of the catheter assembly, which may face skin of the patient.

In some embodiments, the needle cover may be removably coupled to the catheter assembly. In some embodiments, the needle cover may be placed on the catheter assembly during assembly of the catheter system and removed from the catheter system prior to insertion of the catheter system into the vasculature of the patient. In some embodiments, an inner surface of the needle cover and/or an outer surface of the catheter assembly may facilitate securement of the needle cover on the catheter assembly and/or removal of the needle cover from the catheter assembly with a low amount of force by the clinician or manufacturer. In further detail, in some embodiments, the inner surface of the needle cover and/or the outer surface of the catheter assembly may decrease a surface area of the needle cover in contact with the catheter assembly when the needle cover is removably coupled to the catheter assembly. For example, the inner surface of the needle cover may be ribbed. Additionally or alternatively, in some embodiments, the catheter assembly may include the bump and/or the other bump.

In some embodiments, the needle cover may be removably coupled to the catheter assembly via an interference or friction fit. In some embodiments, the inner surface of the needle cover may contact one or more of the following in the friction fit: a portion of the nose, the bump, and the other bump. In some embodiments, the needle cover may be tubular, with a closed or open proximal end.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
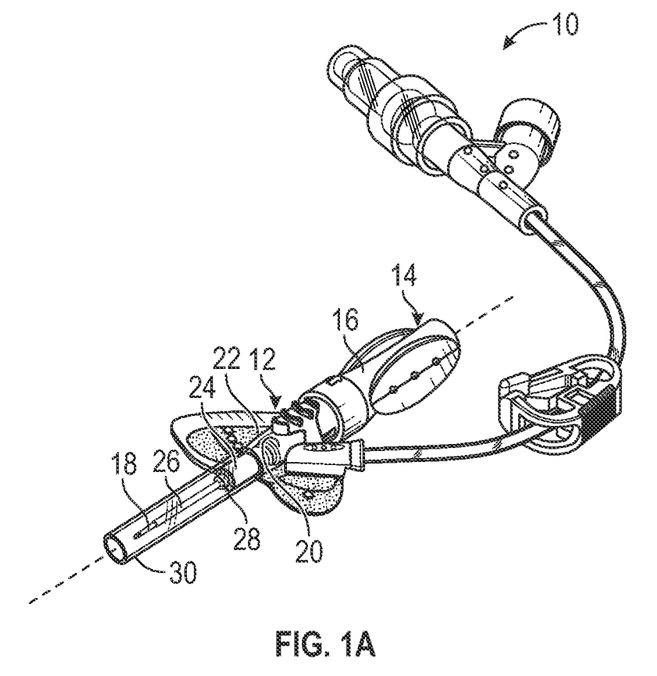
FIG. 1A is an upper perspective view of an example catheter system, according to some embodiments.
Figure 1B:
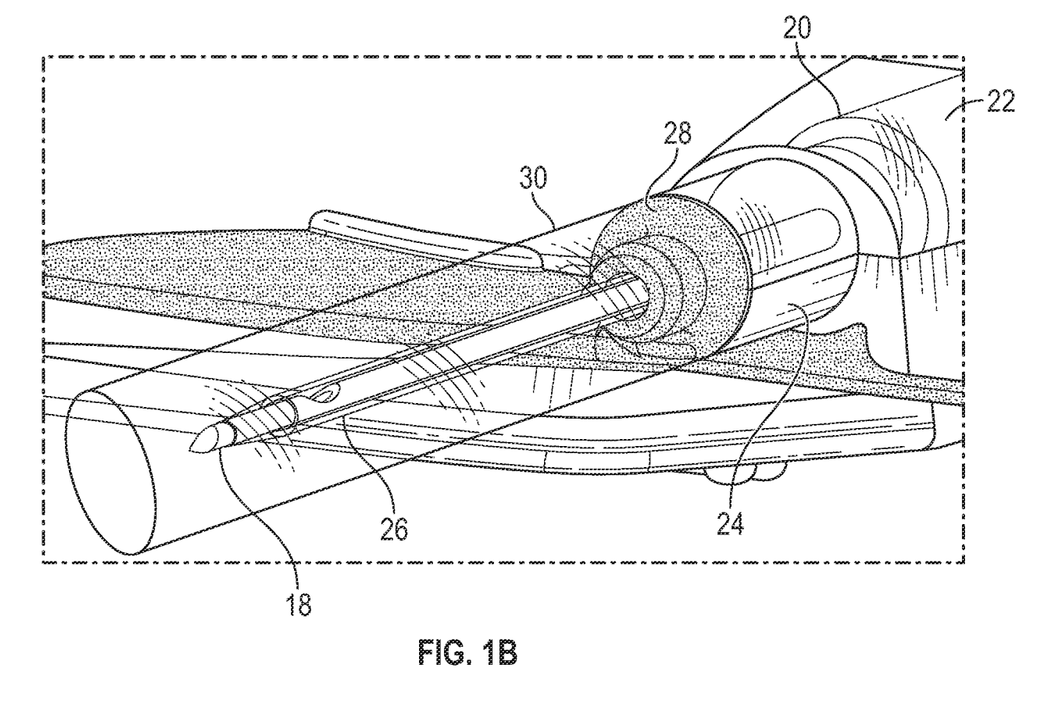
FIG. 1B is an enlarged upper perspective view of a distal portion of the catheter system, according to some embodiments.

Referring now to FIGS. 1A-1B, in some embodiments, a catheter system 10 may include a catheter assembly 12 and a needle assembly 14 coupled to the catheter assembly 12. In some embodiments, the needle assembly 14 may include a needle hub 16 and an introducer needle 18. In some embodiments, a proximal end of the introducer needle 18 may be secured within the needle hub 16. In some embodiments, the introducer needle 18 may include a sharp distal tip.

In some embodiments, the catheter assembly 12 may include a catheter adapter 20, which may include a body 22 and a nose 24 extending distally from the body 22. In some embodiments, the catheter assembly 12 may include a catheter 26 secured within the catheter adapter 20 and extending distally beyond the nose 24. In some embodiments, the catheter 26 may include a peripheral intravenous catheter (PIVC), a midline catheter, or a peripherally-inserted central catheter.

In some embodiments, the introducer needle 18 may extend through the catheter 26. In some embodiments, in response to the introducer needle 18 and/or the catheter 26 being inserted into vasculature of a patient, the introducer needle 18 may be proximally withdrawn from the catheter 26 and removed from the catheter assembly 12. In some embodiments, the catheter 26 may remain within the vasculature of the patient for blood draw and/or fluid infusion.

In some embodiments, the nose 24 may be cylindrical or generally cylindrical. In some embodiments, the nose 24 may be constructed of a rigid or semi-rigid material. In some embodiments, a distal end of the nose 24 may be coupled to a strain relief element 28 at least partially surrounding the catheter 26 and constructed of a compliant or flexible material. In some embodiments, the flexible material may include an elastomer, such as a thermoplastic elastomer or another suitable elastomer. In some embodiments, the strain relief element 28 may extend distally from the nose 24 and form a distal-most portion end of the catheter adapter 12.

In some embodiments, a needle cover 30 may be removably coupled to the catheter assembly 12. In some embodiments, the needle cover 30 may be removably coupled to the catheter assembly 12 via an interference or friction fit. In some embodiments, the needle cover 30 may be placed on the catheter assembly 12 during assembly of the catheter system 10 and removed from the catheter system 10 prior to insertion of the catheter system 10 into the vasculature of the patient. In some embodiments, the needle cover 30 may extend around the nose 24.

Figure 2A:
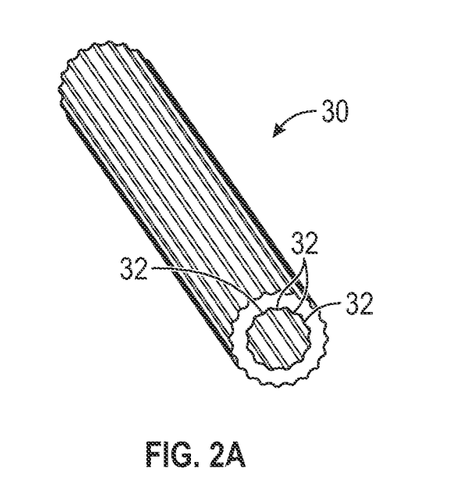
FIG. 2A is an upper perspective view of an example needle cover, according to some embodiments.
Figure 2B:
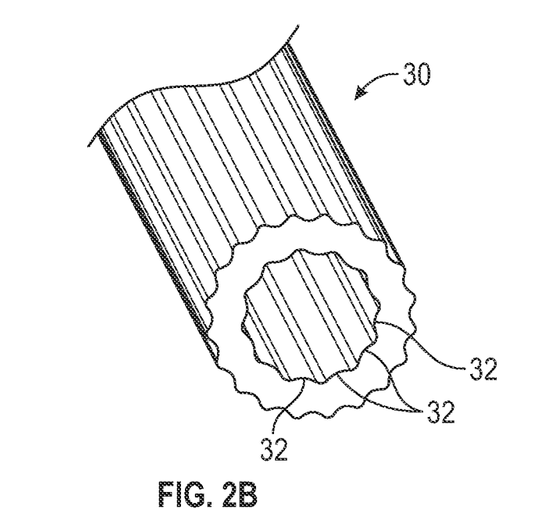
FIG. 2B is an enlarged upper perspective view of a proximal end of the needle cover, according to some embodiments.
Figure 2C:
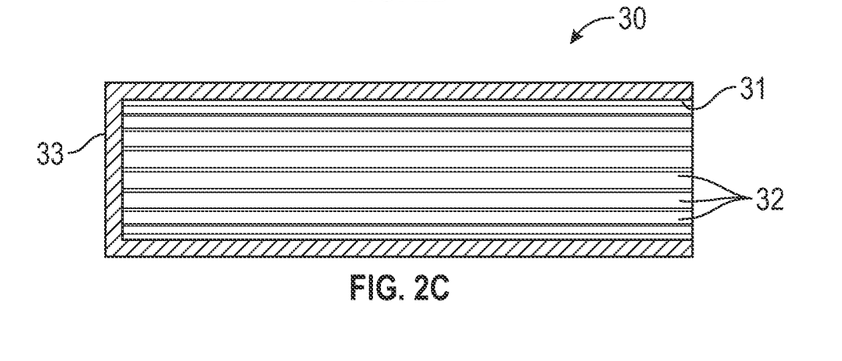
FIG. 2C is a cross-sectional view of the needle cover, according to some embodiments.
Figure 3A:
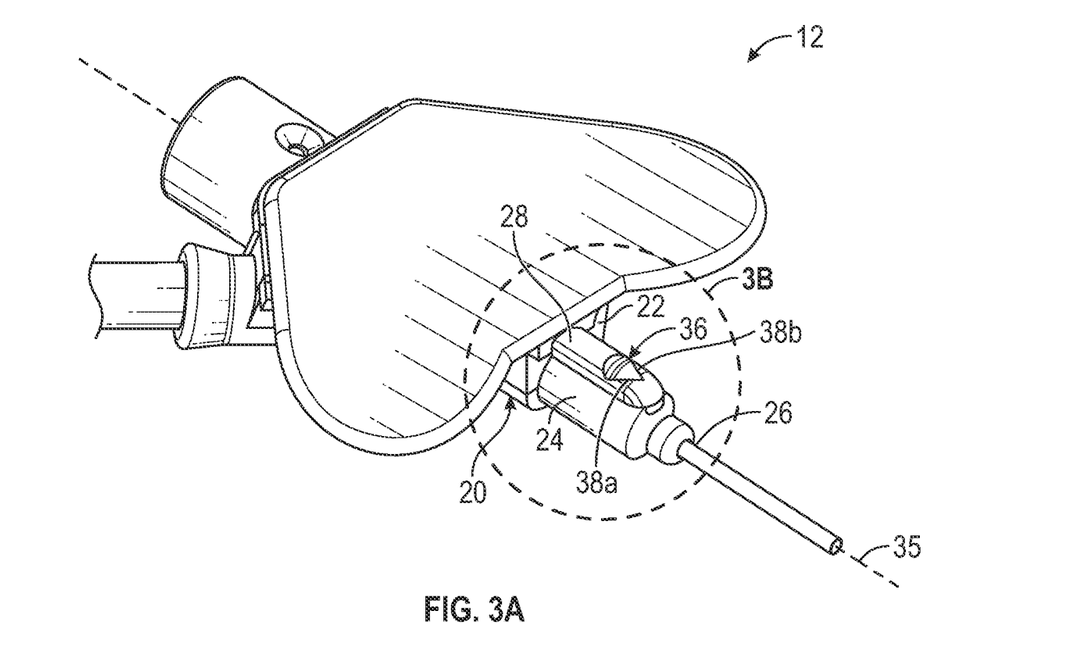
FIG. 3A is a lower perspective view of a portion of an example catheter assembly of the catheter system, according to some embodiments, illustrating the needle cover removed and an example bump.
Figure 3B:
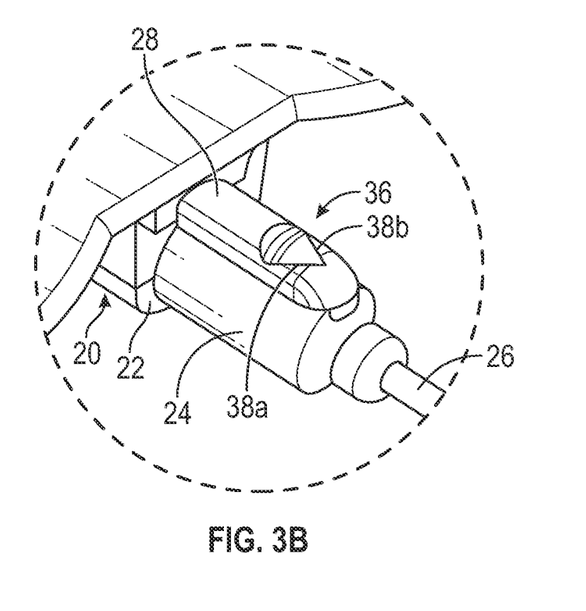
FIG. 3B is an enlarged lower perspective view of a portion of the catheter assembly of the catheter system, illustrating the needle cover removed and the bump, according to some embodiments.
Figure 3C:
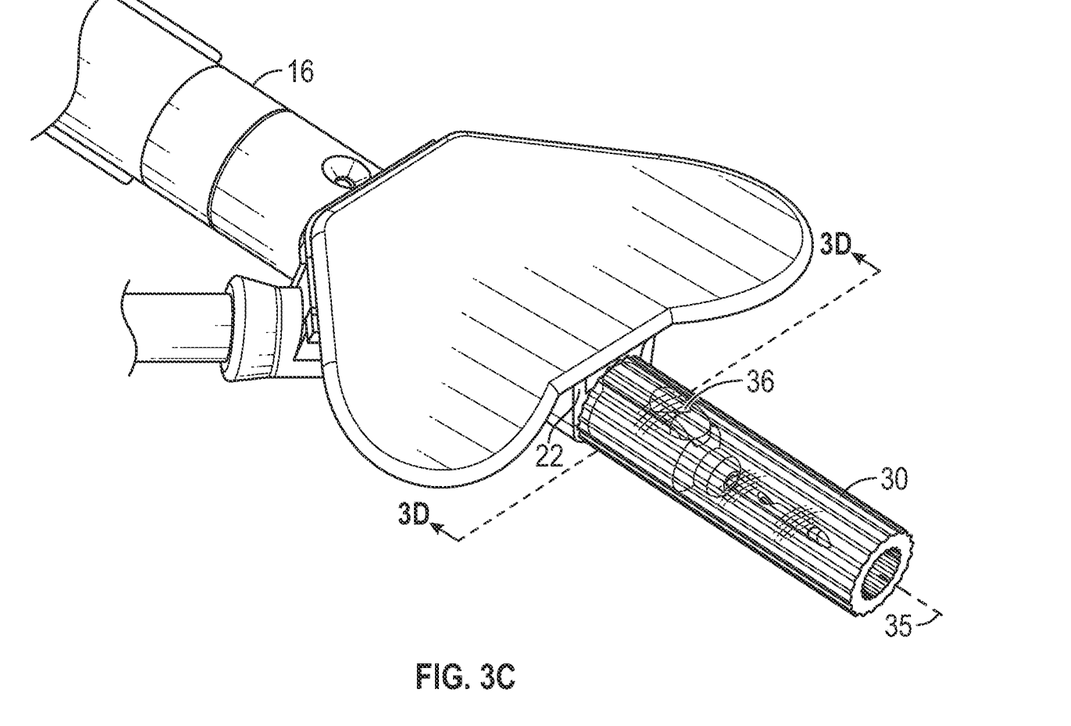
FIG. 3C is a lower perspective view of the catheter system, illustrating the bump, according to some embodiments.
Figure 3D:
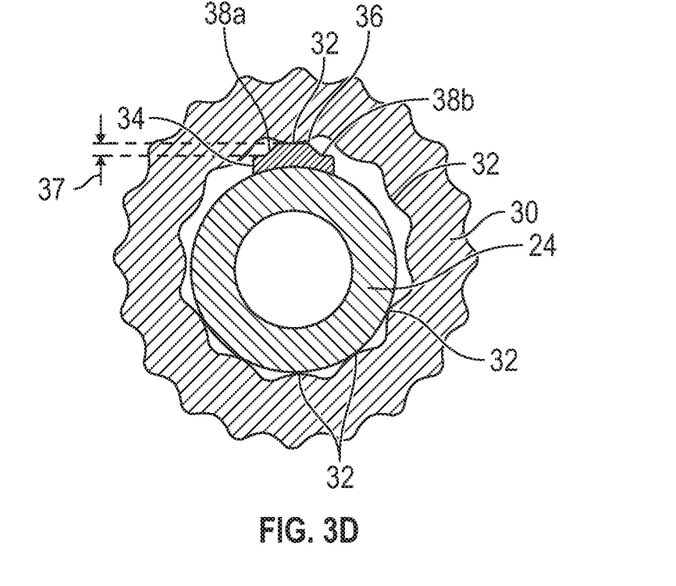
FIG. 3D is a cross-sectional view of the catheter system along the line 3D-3D of FIG. 3C, according to some embodiments.
Figures 4A, 4B:
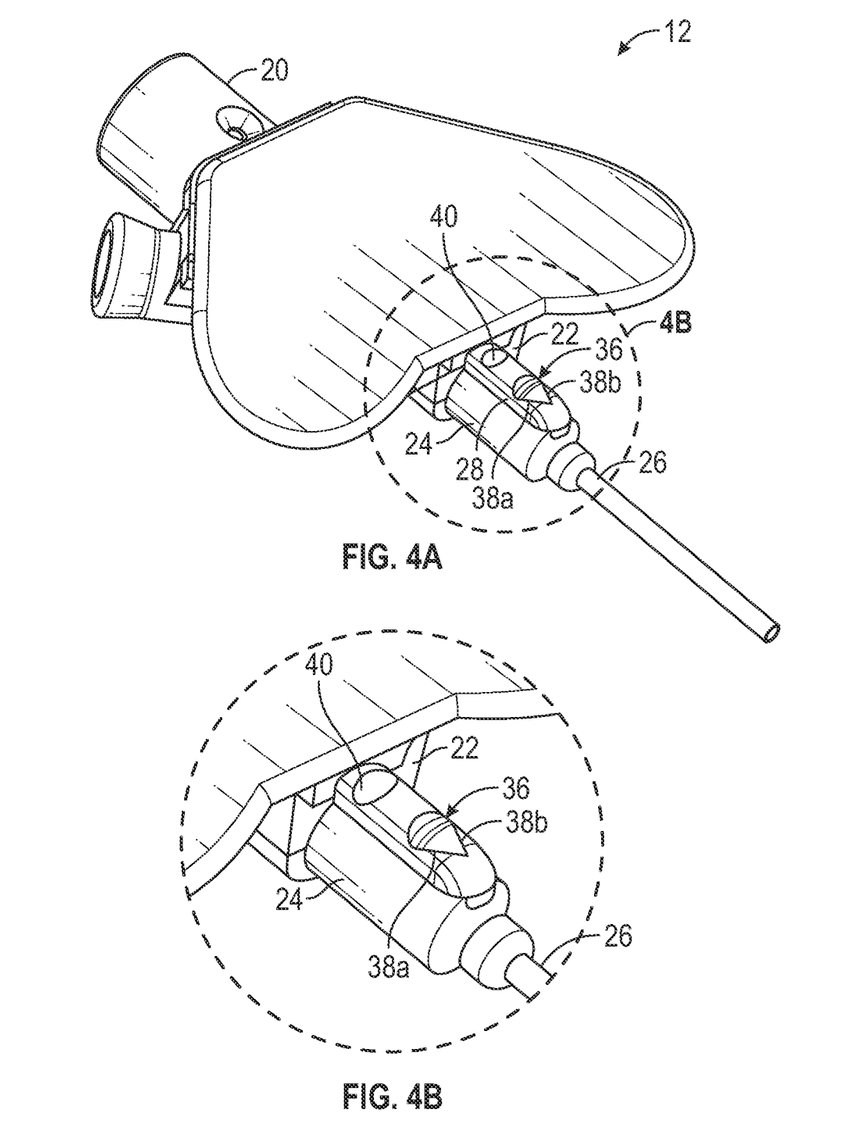
FIG. 4A is a lower perspective view of the catheter assembly, illustrating the needle cover removed and an example other bump, according to some embodiments.
FIG. 4B is an enlarged lower perspective view of a portion of the catheter assembly of the catheter system, illustrating the needle cover removed and the other bump, according to some embodiments.
Figure 4C:
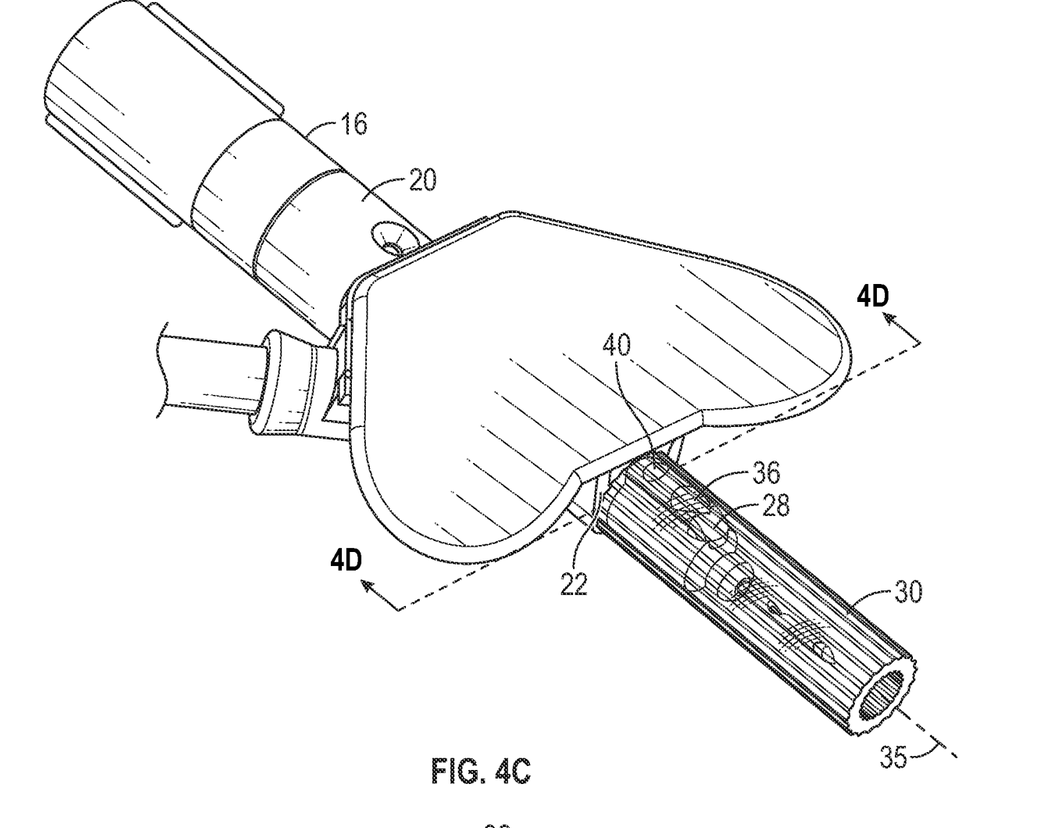
FIG. 4C is a lower perspective view of the catheter system, illustrating the other bump, according to some embodiments.
Figure 4D:
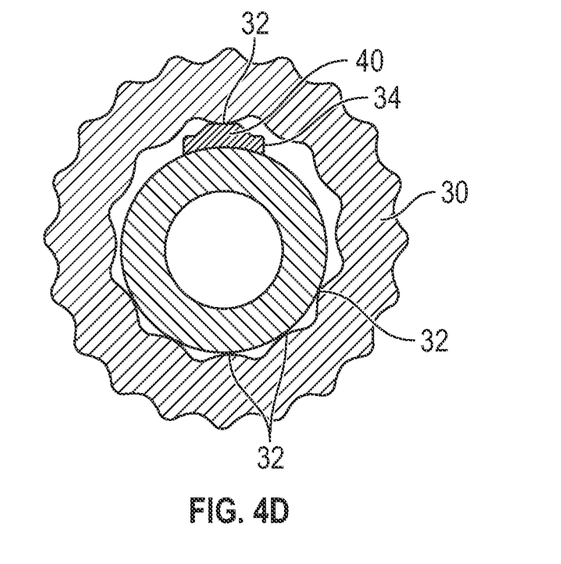
FIG. 4D is a cross-sectional view of the catheter system along the line 4D-4D of FIG. 4C, according to some embodiments.

Referring now to FIGS. 2A-2C, in some embodiments, an inner surface 31 of the needle cover 30 may facilitate securement of the needle cover 30 on the catheter assembly 12 (see, or example FIG. 1A, 3A, or 4A) and/or removal of the needle cover 30 from the catheter assembly 12 with a low amount of force by the clinician or manufacturer. In further detail, in some embodiments, the inner surface 31 of the needle cover 30 may include multiple ribs 32, which may decrease a surface area of the needle cover 30 in contact with a portion of the catheter assembly 12, such as the nose 24, for example. In some embodiments, when the needle cover 30 is secured to the catheter assembly 12, the ribs 32 may contact the portion of the catheter assembly 12, but multiple portions of the inner surface 31 between the ribs 32 may not contact the portion of the catheter assembly 12.

In some embodiments, the needle cover 30 may be generally tubular. In some embodiments, a proximal end 33 of the needle cover 30 may be closed, as illustrated, for example, in FIG. 2C, which may provide protection from the sharp distal tip of the introducer needle 18. In other embodiments, the proximal end 33 of the needle cover 30 may be open.

Referring now to FIGS. 3A-3D, in some embodiments, a strain relief rib 34 may be disposed on the nose 24. In some embodiments, multiple strain relief ribs may be disposed on the nose 24. In some embodiments, the strain relief rib 34 may be generally aligned with a longitudinal axis 35 of the catheter system 10.

In some embodiments, the strain relief rib 34 may be constructed of the flexible material. In some embodiments, a distal end of the nose 24 may be coupled to the strain relief element 28 at least partially surrounding the catheter 26 and constructed of the flexible material or another suitable flexible material.

In some embodiments, a bump 36 may be disposed on the strain relief rib 34. In some embodiments, the bump 36 may be constructed of the flexible material or another suitable flexible material. In some embodiments, a distal end of the bump 36 may include a first side 38a and a second side 38b. In some embodiments, the first side 38a and the second side 38b may be proximate the strain relief rib 34. In some embodiments, the first side 38a and the second side 38b may be angled toward each other, such that the distal end of the bump 36 is tapered in a distal direction, which may facilitate lead-in or smooth movement of the needle cover 30 with respect to the catheter assembly 12.

In some embodiments, the distal end of the bump 36 may be tapered in the distal direction toward a central axis of the bump 36, which may be aligned with the longitudinal axis 35 of the catheter system 10. In some embodiments, a height 37 of the distal end of the bump 36 may decrease in the distal direction. In some embodiments, the bump 36 may contact one or more of the ribs 32 of the needle cover 30, decreasing the surface area of the needle cover 30 in contact with the catheter assembly 12.

Referring now to FIGS. 4A-4D, in some embodiments, the bump 36 and/or another bump 40 may be disposed on the strain relief rib 34. In some embodiments, the bump 36 and/or the other bump 40 may be constructed of the flexible material or another suitable flexible material. In some embodiments, one or more of the following may be monolithically formed as a single unit: the strain relief rib 34, the bump 36, the other bump 40, and the strain relief element.

In some embodiments, the bump 36 may be aligned with the other bump 40. In some embodiments, the bump 36 may be distal to the other bump 40. In some embodiments, one or more of the following may be disposed on a bottom of the catheter assembly 12: the strain relief rib 34, the bump 36, and the other bump 40. In some embodiments, a bevel of the introducer needle 18 may face upwardly, away from the bottom of the catheter assembly 12, which may face skin of the patient.

In some embodiments, an outer surface of the catheter assembly 12 may facilitate securement of the needle cover 30 on the catheter assembly 12 and/or removal of the needle cover 30 from the catheter assembly 12 with a low amount of force by the clinician or manufacturer. In further detail, in some embodiments, the outer surface of the catheter assembly 12 may decrease a surface area of the needle cover 30 in contact with the catheter assembly 12 when the needle cover 30 is removably coupled to the catheter assembly 12. For example, the catheter assembly may include the bump 36 and/or the other bump 40. In some embodiments, the inner surface 31 of the needle cover 30 may contact one or more of the following in the friction fit: a portion of the nose 24, the bump 36, and the other bump 40. In some embodiments, the portion of the nose 24 that the inner surface 31 contacts may be a lower or bottom portion of the nose 24, which may be opposite the bump 36 and/or the other bump 40.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a catheter secured within a catheter adapter and extending distally beyond a generally cylindrical nose;
   the catheter adapter comprising:
      a body;
      the generally cylindrical nose extending distally from the body and comprising a distal end and a proximal end, wherein the generally cylindrical nose is constructed of a first material;
      a strain relief rib extending outwardly from the generally cylindrical nose and along a length between the distal end of the generally cylindrical nose and the proximal end of the generally cylindrical nose, wherein the strain relief rib is constructed of a second material more flexible than the first material, wherein the strain relief rib no more than partially surrounds the catheter, wherein the strain relief rib comprises a distal end and a proximal end, wherein a width of the proximal end of the strain relief rib is less than a width of the generally cylindrical nose;
      a bump disposed on the strain relief rib and extending outwardly from the strain relief rib; and
      another bump aligned with the bump along a longitudinal axis of the catheter system and extending outwardly from the strain relief rib, wherein the bump and the other bump are constructed of the second material.

2. The catheter system of claim 1, wherein the strain relief rib, the bump, and the other bump are monolithically formed as a single unit.

3. The catheter system of claim 1, wherein the bump is distal to the other bump.

4. The catheter system of claim 1, wherein the distal end of the bump comprises a first side and a second side proximate the strain relief rib, wherein the first side and the second side are angled toward each other.

5. The catheter system of claim 1, wherein a height of a distal end of the bump decreases in a distal direction.

6. The catheter system of claim 1, wherein the strain relief rib and the bump are disposed on a bottom of the catheter adapter and aligned with a longitudinal axis of the catheter adapter.

7. The catheter system of claim 1, wherein the second material is a flexible material.

8. The catheter system of claim 1, further comprising a needle assembly, comprising a needle hub and an introducer needle secured within the needle hub and extending through the catheter, wherein the needle hub is coupled to the catheter adapter.

9. The catheter system of claim 1, further comprising a needle cover removably coupled to the catheter adapter, wherein an inner surface of the needle cover comprises a plurality of ribs and contacts the bump.

10. The catheter system of claim 9, wherein the needle cover is removably coupled to the catheter adapter via a friction fit.

11. The catheter system of claim 9, wherein the needle cover is tubular.

12. The catheter system of claim 1, wherein the second material comprises an elastomer.

13. The catheter system of claim 1, wherein the generally cylindrical nose is constructed of a rigid or semi-rigid material.

14. The catheter system of claim 1, wherein the strain relief rib is generally aligned with a longitudinal axis of the catheter adapter.

15. The catheter system of claim 1, wherein the distal end of the generally cylindrical nose is coupled to the strain relief rib no more than partially surrounding the catheter and constructed of a flexible material.

16. The catheter system of claim 1, wherein the generally cylindrical nose is cylindrical, wherein the strain relief rib extends along the length between the distal end of the generally cylindrical nose and the proximal end of the generally cylindrical nose, wherein the strain relief rib comprises a first side opposite a second side, wherein the first side and the second side are generally parallel to a longitudinal axis of the catheter system.

17. A catheter system, comprising:
a catheter secured within a catheter adapter and extending distally beyond a generally cylindrical nose;
the catheter adapter, comprising:
  a body;
  the generally cylindrical nose extending distally from the body and comprising a distal end and a proximal end;
  a strain relief rib disposed on the generally cylindrical nose, wherein the strain relief rib extends outwardly from the generally cylindrical nose and along a length between the distal end of the generally cylindrical nose and the proximal end of the generally cylindrical nose, wherein the strain relief rib no more than partially surrounds the catheter, wherein the strain relief ribs comprises a distal end, a proximal end, and a length extending from the distal end of the strain relief rib to the proximal end of the strain relief rib, wherein a width of the strain relief rib along an entirety of the length of the strain relief rib is less than a width of the generally cylindrical nose, wherein the strain relief rib is constructed of a flexible material;
  a bump disposed on the strain relief rib; and
  another bump aligned with the bump along a longitudinal axis of the catheter system, wherein the bump and the other bump extend outwardly from the catheter system further than the strain relief rib; and
a needle cover removably coupled to the catheter adapter, wherein a first portion of an inner surface of the needle cover contacts the bump and the other bump, wherein a second portion of the inner surface of the needle cover contacts the generally cylindrical nose.

18. A catheter system, comprising:
a catheter secured within the catheter adapter and extending distally beyond a generally cylindrical nose;
a catheter adapter comprising:
  a body;
  the generally cylindrical nose extending distally from the body and comprising a distal end and a proximal end, wherein the generally cylindrical nose is constructed of a first material;
  a strain relief rib extending outwardly from the generally cylindrical nose and along a length between the distal end of the generally cylindrical nose and the proximal end of the generally cylindrical nose, wherein the strain relief rib no more than partially surrounds the catheter, wherein the strain relief rib comprises a distal end and a proximal end, wherein a width of the proximal end of the strain relief rib is less than a width of the generally cylindrical nose, wherein the strain relief rib is constructed of a second material more flexible than the first material.

19. The catheter system of claim 18, further comprising a needle cover removably coupled to the catheter adapter, wherein a first portion of an inner surface of the needle cover contacts a bump and another bump wherein a second portion of the inner surface of the needle cover contacts the generally cylindrical nose.

* * * * *